US010309820B2

(12) United States Patent
Ott et al.

(10) Patent No.: US 10,309,820 B2
(45) Date of Patent: Jun. 4, 2019

(54) METHOD AND DEVICE FOR DISTINGUISHING BETWEEN A FOAM AND/OR LIQUID CONTACTING

(71) Applicant: TECAN Trading AG, Mannedorf (CH)

(72) Inventors: Philipp Ott, Steg im Tosstal (CH); Lars Kamm, Schanis (CH); Markus Schöni, Nanikon (CH); Remo Keller, Rapperswil (CH); Paul Zbinden, Wolfhausen (CH)

(73) Assignee: TECAN TRADING AG, Mannedorf (CH)

(*) Notice: Subject to any disclaimer, the term of this patent is extended or adjusted under 35 U.S.C. 154(b) by 714 days.

(21) Appl. No.: 14/806,036

(22) Filed: Jul. 22, 2015

(65) Prior Publication Data
US 2016/0025546 A1 Jan. 28, 2016

(30) Foreign Application Priority Data

Jul. 24, 2014 (CH) ...................................... 1129/14

(51) Int. Cl.
*G01N 35/10* (2006.01)
*G01F 23/26* (2006.01)
*G01F 23/00* (2006.01)

(52) U.S. Cl.
CPC ........ *G01F 23/266* (2013.01); *G01F 23/0061* (2013.01); *G01F 23/265* (2013.01); *G01N 35/1011* (2013.01); *G01N 2035/1018* (2013.01)

(58) Field of Classification Search
CPC .............................................. G01N 2035/1018
See application file for complete search history.

(56) References Cited

U.S. PATENT DOCUMENTS

| 5,319,954 A | * | 6/1994 | Koeda ................ G01N 35/1016 73/19.1 |
| 5,866,426 A | * | 2/1999 | Ball ....................... G01F 23/265 340/620 |
| 2007/0144253 A1 | | 6/2007 | Kobayashi |
| 2011/0000296 A1 | | 1/2011 | Muerset |

FOREIGN PATENT DOCUMENTS

| CH | 702427 A1 | 6/2011 |
| DE | 10157762 A1 | 6/2003 |
| EP | 1048953 A2 | 11/2000 |

* cited by examiner

*Primary Examiner* — Lisa M Caputo
*Assistant Examiner* — Alex T Devito
(74) *Attorney, Agent, or Firm* — Notaro, Michalos & Zaccaria P.C.

(57) ABSTRACT

A method and device for distinguishing between a contacting of foam (2) or of liquid (1) in a liquid container (5) of a device (100) by employing a capacitively operating measuring device (M) having a sensor (3) which can be moved up and down in the liquid container (5), in which at least one output signal ($s_{out}(t)$) is processed by the measuring device (M).

15 Claims, 3 Drawing Sheets

METHOD AND DEVICE FOR DISTINGUISHING BETWEEN A FOAM AND/OR LIQUID CONTACTING

The invention relates to a method and a device for distinguishing between a contacting of a sensor with foam or liquid in a liquid container.

BACKGROUND OF THE INVENTION

There are numerous laboratory systems and medical as well as pharmaceutical devices which require precise pipetting operations in order to obtain satisfactory analytical precisions. For this purpose, the level in test tubes, titre plates and other liquid containers must be determined precisely. There are also applications in which it is a question of detecting foam-liquid phase boundaries. Hereinafter the term of the phase boundary is used both for transitions between gaseous and liquid media (gas-liquid phase boundary) and also for transitions between various liquid media (foam-liquid phase boundary).

Such a determination of the phase boundary is particularly important when it is a question of the automation of measurement or experimental sequences. The so-called level determination is typically made by means of a detection of the liquid level, i.e. the position of the phase boundary between air and liquid is determined. This process is also designated as "Liquid Level Detection" (LLD).

In the prior art, various methods for level determination are known, which are based on different physical principles such as, for example, detection of the light reflected from the surface of the liquid or measurement of electrical properties of pipettes when they are brought in contact with the liquid. Since a gas and a liquid have significantly different dielectric constants, the gas-liquid phase boundary can also be determined by means of a capacitance change.

Liquid Level Detection is used, for example, in pipetting devices. Here when sucking in with a pipette, the pipetting needle should be immersed as little as possible into the liquid to be pipetted in order to keep any contamination with sample liquid as low as possible. During sucking in, the pipetting needle is therefore typically immersed only a few millimeters below the liquid level. However, it must be ensured that the pipetting needle is immersed sufficiently far and therefore no air can be sucked in. During the sucking in process, the pipetting is then continuously tracked to the decreasing liquid level so that it always remains immersed to the same depth in relation to the liquid level. After the sucking-in, it can then be calculated, e.g. by means of the sucked-in volume and the cross-sectional area of the liquid container, at which height the gas-liquid phase boundary should be located. During emergence of the pipetting tip, an emergence signal can then be compared with the calculated position of the gas-liquid phase boundary in order to thus verify the pipetting process.

On the one hand, it is therefore desirable to position the pipetting tip just below the liquid surface, on the other hand the level can vary substantially from one liquid container to another, which is why the pipetting tip must be positionable precisely. For this it is extremely important to be able to correctly detect the liquid surface.

In some cases however, the reliability of the detection of the liquid surface with the known methods is not satisfactory, in particular in the case of liquids which are liable to foam formation.

Therefore it is important to be able to distinguish between a foam and/or liquid contacting of a sensor which can be delivered in a liquid container.

OBJECT OF THE INVENTION

It is therefore the object to provide a method for distinguishing between a contacting of a movable sensor with foam or with liquid in a liquid container of a (laboratory) device, which enables a reliable detection of at least one foam phase boundary.

A further object of the invention is to provide a method for a detection of the transition of the sensor from foam to liquid.

A further object of the invention is to provide corresponding devices.

DISCLOSURE OF THE INVENTION

The above-identified technical object of the invention is solved by a method
  for detecting a contacting of a movable sensor with foam or with liquid and
  for distinguishing between a contacting of a movable sensor with foam or with liquid in a liquid container.

In both cases, a capacitively operating measuring device is used which is connectable to a sensor which can be moved up and down. During movement of the sensor at least one output signal is processed by the measuring device. The method according to the invention comprises the following steps which need not necessarily be executed successively:
a. executing an up or down movement of the sensor in the liquid container;
b. applying an input signal having a first frequency to the sensor;
c. applying the input signal having a second frequency to the sensor, where the second frequency and the first frequency are different;
d. within the framework of a first process—evaluating the output signal in order to detect a first jump of the output signal;
e. within the framework of a second process—evaluating the output signal in order to detect a second jump of the output signal,
f. comparing the first jump ($\Delta X1$) with the second jump ($\Delta X2$);
g. if the comparison exceeds a specification, outputting an identifier (Ks), which signals a contacting of the sensor (3) with foam (2) in the liquid container (5).

Preferably in all embodiments, in the comparison in step f. the quotient of the first jump and the second jump is determined, and in step g. the identifier (Ks) is output if the quotient exceeds a factor (F). The factor (F) here corresponds to the specification.

Preferably in all embodiments, the steps b. and d. as well as the steps c. and e. are correlated with one another, i.e. the first jump is correlated to the first frequency and the second jump is correlated to the second frequency.

According to the invention, the presence of a phase boundary can be identified by means of an examination of the signal jumps. This is preferably accomplished in all embodiments within the framework of the first and second process. Preferably in all embodiments, steps f. and g. are only executed after the presence of a phase boundary has been identified. Steps f. and g. are also designated here as third process.

The above-identified further technical object of the invention is solved by a method wherein after outputting the identifier which signals a contacting of the sensor with foam, the following steps are executed (these further steps are optional):

a. executing a further movement of the sensor in the previously executed direction of movement;
b. within the framework of a fourth process—applying an input signal to the sensor and evaluating the output signal in order to identify a foam-liquid phase boundary and optionally outputting an identifier which signals a transition of the sensor from foam into liquid.

In preferred embodiments of the invention, the following procedure is used:
1. detecting a phase boundary between gas/foam or gas/liquid (this is accomplished here by executing the first and second process).
2. determining whether immersion has taken place into liquid or foam. That is, in this process phase a distinction is made between a gas/foam and a gas/liquid phase boundary. This is accomplished according to the invention by examining/evaluating the quotient (this is accomplished here by executing the third process).
3. (optional): detecting the phase boundary between foam and liquid if a gas/foam phase boundary has been identified under Point 2. (this is accomplished here by executing the fourth process).

The technical object of the invention is also solved by a device whose features can be deduced from the corresponding claims.

Advantageous Effects

The most important advantage of the invention is that when delivering a sensor (e.g. in the form of a pipette) a distinction can be reliably made between foam or liquid contacting. It can thus be ensured that, for example, a level measurement yields correct data and/or that, e.g. a pipetting process can be carried out without the risk of air being sucked in.

BRIEF DESCRIPTION OF THE DRAWINGS

The method according to the invention is now explained in detail with reference to schematic drawings of exemplary embodiments which do not restrict the scope of the invention.

DETAILED DESCRIPTION OF THE PREFERRED EMBODIMENTS

Figure 1:
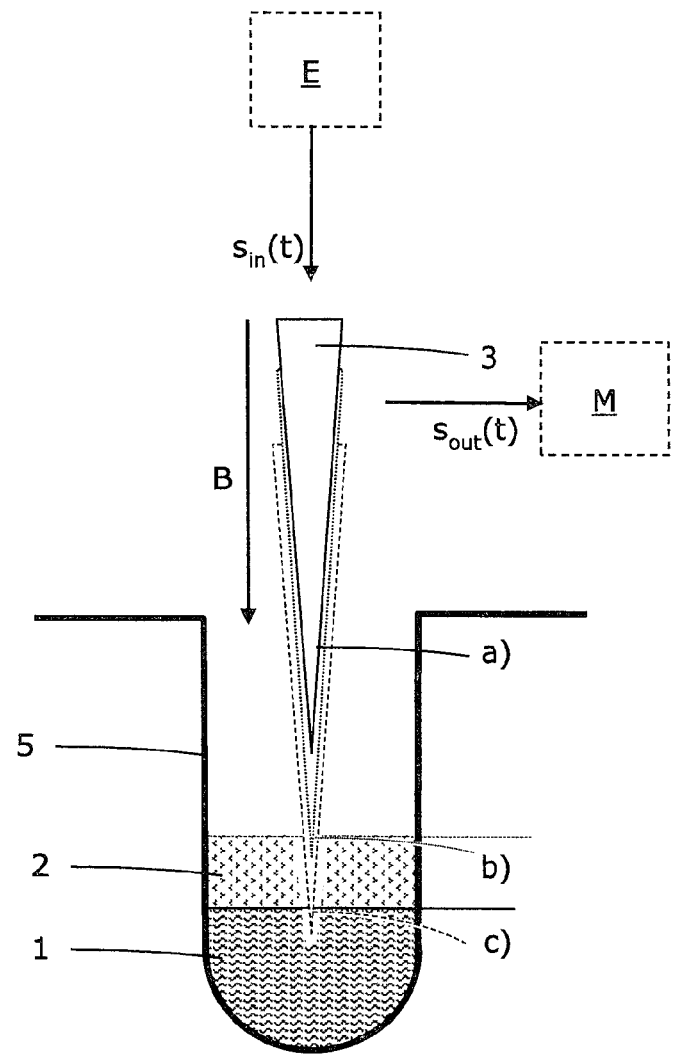
FIG. 1 shows a schematic illustration of the detection method according to the invention which shows a pipette at three different delivery depths.

Advantageous embodiments of the invention are described hereinafter, where these are exemplary embodiments. These comprise both different configurations of the overall invention and also assemblies and individual parts of the invention. In principle, the assemblies and individual parts of the various embodiments described can be combined with one another or the assemblies and individual parts of the individual embodiments can be replaced by the assemblies and individual parts of other embodiments. The combinations formed thereby can necessitate smaller adaptations familiar to every person skilled in the art and therefore not described further, for example, in order to enable an interaction or intermeshing of the assemblies and individual parts.

The term phase boundary is used for boundaries between two or more media which have different dielectric constants. This is especially a question of liquid-liquid and gas-liquid phase boundaries.

The term module is used here to describe a functional group which is implemented in hardware, software or as a combination of hard—and software.

The term "identifier" is used here for a code, a code word, a signal, a memory entry or a flag which is set. Such an identifier can, for example, acquire a logic "0" or a logic "1".

In connection with the present invention there is variously talk of devices 100. These are preferably laboratory devices and other systems, installations, apparatus, handling centres and the like which are equipped with means for determining a phase boundary. The device according to the invention is an element or a component of such an item of laboratory device. A laboratory device 100 can, for example, comprise a plurality of identical devices or a plurality of different devices.

The method according to the invention is preferably configured in all embodiments to distinguish between a foam or liquid contacting of a sensor 3 (e.g. a pipette serving as a sensor) in a liquid container 5. Hereinafter reference is made to the use of pipettes, wherein other (pipette) tips, needles, tubes and the like are suitable as sensor 3 and can be used within the framework of the invention.

Hereinafter reference is made to the execution of a delivery movement. Such a delivery movement can describe a downwards or an upwards movement of the sensor 3 in the liquid container 5.

Preferably a pipette 3 which can be delivered in the direction of the liquid 1 in the liquid container 5 is used for the purpose of detecting.

FIG. 1 shows a schematic illustration of the detection method according to the present invention, wherein the pipette 3 is shown at three different delivery depths along the delivery direction B, namely: a) before immersion into the liquid 1/the foam 2; b) during immersion into foam 2; and c) during immersion into liquid 1. During the delivery movement B of the pipette 3 in the direction of the liquid 1 and/or the foam 2, an input signal $s_{in}(t)$ is applied to the pipette 3. When the tip of the pipette 3 touches the liquid/foam surface, the capacitance between the pipette 3 and the liquid 1 or the foam 2 disappears abruptly. This leads to an evaluable jump in the overall capacitance. The pipette 3 here serves, as it were, as a measuring electrode of a measuring device M. An output signal $s_{out}(t)$ can be tapped at the pipette. The application of the input signal $s_{in}(t)$ and the tapping of the output signal $s_{out}(t)$ is indicated schematically in FIG. 1.

These aspects are described in detail hereinafter with reference to specific embodiments.

Figure 2:
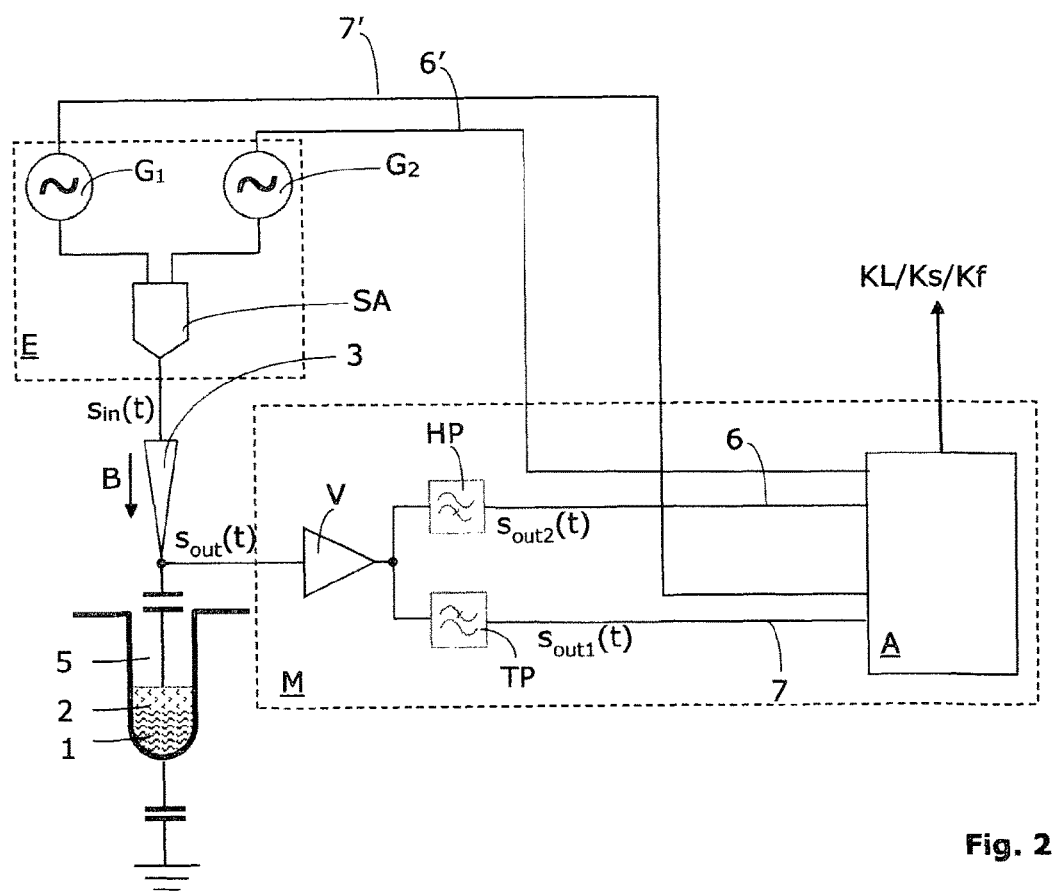
FIG. 2 shows a schematic circuit diagram of a first embodiment of an input signal generator and a capacitively operating measuring device according to the present invention.

FIG. 2 shows a schematic circuit diagram of a first embodiment of the input signal generator E and the capacitively operating measuring device M according to the present invention. The pipette 3 forms a capacitor together with the foam/liquid surface, where the air forms the dielectric between the plates of this capacitor. The tip of the pipette 3 forms, as it were, the first part of the measuring capacitor with two capacitor plates, the liquid or foam surface forms the second part with an interposed air-dielectric, where the plate spacing of the capacitor plates is variable according to the position of the pipette 3. During contact of the foam/liquid surface with the tip of the pipette 3, the mentioned jump of the total capacitance is obtained.

The input signal generator E comprises, for example, a first alternating voltage generator $G_1$ for generating a first voltage component and a second alternating voltage generator $G_2$ for generating a second voltage component respectively. The first and second voltage components are preferably sinusoidal.

In a preferred embodiment of the invention, by means of the first alternating voltage generator $G_1$ or the second alternating voltage generator $G_2$, a first sinusoidal signal $S_1$ having a first frequency $f_1$ and a second sinusoidal signal $S_2$ having a second frequency $f_2$ is applied as input signal $s_{in}(t)$ to the pipette 3, where these two frequencies $f_1$ and $f_2$ differ from each other.

In preferably all embodiments the (base) frequency $f_1$ lies in the range between 10 kHz and 1 MHz. In preferably all embodiments, the (foam) frequency $f_2$ lies a factor of 5 to 100 higher than the frequency $f_1$.

An optional voltage adder SA is provided for the superposition of the first $S_1$ or second sinusoidal signal $S_2$. The first alternating voltage generator $G_1$ and the second alternating voltage generator $G_2$ as well as the voltage adder SA can, at least functionally, be combined to form an input signal generator E, which generates a resulting alternating voltage composed of two alternating voltage components. The resulting alternating voltage is applied as input signal $s_{in}(t)$ to the sensor 3 (pipette 3) which in all embodiments serves as measuring electrode.

Naturally, other types of voltage generators 4 known per se can also be used for the method according to the invention. Thus, it is not absolutely necessary to generate two sinusoidal alternating voltage components with two partial alternating voltage generators $G_1$, $G_2$. Alternatively, for example, an alternating voltage can be generated in the form of other periodic signals.

Whilst the input signal $s_{in}(t)$ is applied by the input signal generator E to the sensor 3, the output signal $s_{out}(t)$ of the sensor 3 is processed/evaluated by means of an evaluating circuit A in order to detect a capacitance variation and/or impedance variation. For this purpose the evaluating circuit A is located downstream of the sensor 3, i.e. in all embodiments the evaluating circuit A can be connected in terms of circuitry to the sensor 3. In the exemplary embodiment of FIG. 2 the evaluating circuit A or the measuring device M, respectively, initially includes an amplifier V for amplifying the output signal $s_{out}(t)$.

The output signal of the amplifier V is here, for example, supplied to a diplexer which splits the output signal $s_{out}(t)$ in to a first output signal component $s_{out1}(t)$—corresponding to the first frequency $f_1$ and a second output signal component $s_{out2}(t)$—corresponding to the second frequency $f_2$—and guides these components onto a first signal path 6 or a second signal path 7. This can be accomplished, for example, with a high-pass filter HP and a low-pass filter TP which can be parts of the diplexer. The frequency $f_1$ which is assigned to the generator $G_1$ is a lower frequency than the frequency $f_2$. A demodulation can be executed substantially synchronously as a multiplication of the partial signal components by the first voltage component applied to the pipette 3 (from the alternating voltage generator $G_1$) or a second voltage component (from the second alternating voltage generator $G_2$). The demodulation can take place, for example, in an evaluating circuit A to which the signals are supplied as shown in FIG. 2. The supply of the first voltage component and the second voltage component can be accomplished, for example via signal paths 6' and 7'.

Preferably in all embodiments of the invention, the first output signal component $s_{out1}(t)$ is evaluated within a first process $P_1$ and the second output signal component $s_{out2}(t)$ is evaluated within the framework of a second process $P_2$—preferably simultaneously. In all embodiments this evaluation can be made in the evaluation circuit A. As a result, the evaluation circuit A outputs an identifier KL or it provides an identifier KL which can be retrieved from another circuit or a computer. The identifier KL indicates that a phase boundary has been detected between air and a denser medium (foam 2 or liquid 1).

After such a phase boundary has been detected, further processes can follow.

Preferably in all embodiments of the invention after detecting such a phase boundary, a third process P3 is carried out in order to be able to distinguish whether this is an air/liquid or air/foam phase boundary.

Preferably in all embodiments of the invention, within the framework of the third process $P_3$, a first signal jump is related to a second signal jump or the two jumps are compared with one another (e.g. by forming the quotient Q). In this case, the first signal jump is correlated with the first frequency $f_1$ and the second signal jump is correlated with the second frequency $f_2$. As a result, the evaluation circuit A, for example, outputs an identifier Ks or Kf, or it provides an identifier Ks or Kf which can be retrieved from another circuit or a computer. The provision of the corresponding identifiers is symbolized in FIG. 2 by an arrow with the reference number KL/Ks/Kf.

These identifiers can also be provided at separate outputs of the evaluation circuit A in all embodiments.

In all embodiments the evaluation circuit A can comprise an analogue electric circuit and/or a digital circuit with a processor.

In all embodiments the evaluation circuit A can comprise a circuit block for the first and second process $P_1$, $P_2$ and a circuit block for the third process $P_3$. However these circuit blocks can also be combined in terms of circuitry.

Figure 3:
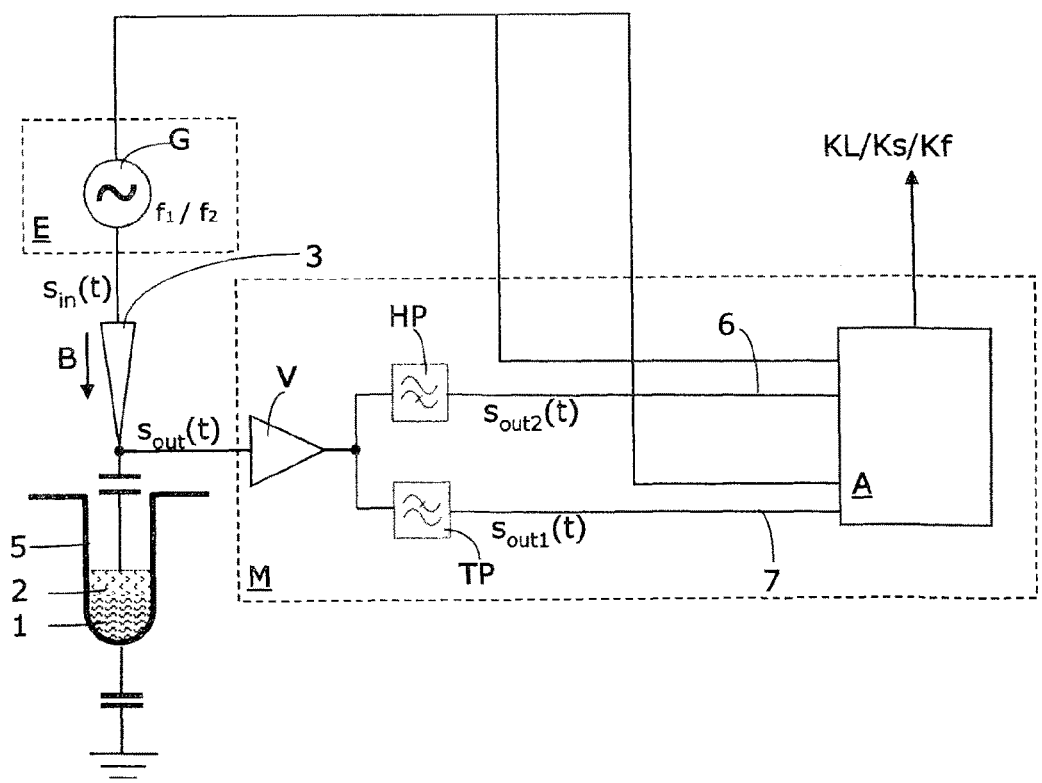
FIG. 3 shows a schematic circuit diagram of a second embodiment of the input signal generator and the capacitively operating measuring device according to the present invention.

FIG. 3 shows a schematic circuit diagram of a second embodiment of the input signal generator E according to the present invention. The difference from the first embodiment of FIG. 2 is that the input signal generator E only comprises a single alternating voltage generator G where a first sinusoidal signal $S_1$ and a second sinusoidal signal $S_2$ are applied alternately as input signal $s_{in}(t)$ quasi-simultaneously to the sensor 3. Accordingly, the output signal $s_{out}(t)$ at the first frequency $f_1$ or the second frequency $f_2$ can be evaluated alternately within the framework of the first process $P_1$ or the second process $P_2$ quasi-simultaneously.

In summary it can be noted that during the execution of a downwards or upwards movement of the sensor 3 an input signal $i_{in}(t)$ is applied to the sensor 3. For this purpose, in all embodiments the sensor can be connected to one of the input signal generators E shown as an example. During the execution of the movement B it is determined whether a jump is obtained in the output signal $s_{out}(t)$. Within the framework of a first process P1 it is determined whether a jump $\Delta X1$ occurs. This involves a jump $\Delta X1$ of the output signal $s_{out}(t)$. If no jump exists $\Delta X1$ (or if the jump is no greater than a jump factor SF), the movement of the sensor 3 is continued further. The direction of movement of the movement B remains the same and the determination as to whether a jump ΔX1 occurs is continued. The presence of such a jump ΔX1 indicates a phase boundary although it cannot yet be identified at this moment whether this is an air/foam or an air/liquid phase boundary.

Within the framework of a second process P2 it is determined whether a jump ΔX2 occurs. This involves a jump ΔX2 of the output signal $s_{out}(t)$. The process P2 can be executed simultaneously to the process P1 or temporally after the process P1. The two processes P1, P2 can overlap one another temporally. The presence of such a jump ΔX2 indicates a phase boundary although it cannot yet be identified at this moment whether this is an air/foam or an air/liquid phase boundary.

In order to obtain additional security, all the embodiments can only output the detection of a phase boundary when two jumps ΔX1 and ΔX2 exist. However the examination of only one jump ΔX1 or ΔX2 is sufficient. Upon identifying such a phase boundary, the identifier KL can be output as already described.

Preferably in all embodiments which are concerned with the detection of foam, the more precise investigation of the jump(s) is only made when a first jump ΔX1 and a second jump ΔX2 have been identified. The more precise investigation serves to be able to distinguish a foam boundary from a liquid boundary. In connection with the corresponding third process P3, the two jumps ΔX1 and ΔX2 are put in a relationship to one another or compared with one another (preferably by forming a quotient Q).

In order to improve the detection accuracy (e.g. whereby signal noise can be distinguished from actual events), a jump factor SF can be predefined which is used by the evaluation circuit A to be able to classify a jumpy change of the output signal $s_{out}(t)$ as jump ΔX1 or ΔX2 in the sense of the invention. One of the circuits E or A in all embodiments can comprise a memory for predefining the jump factor SF.

Within the framework of the more accurate investigation (i.e. in the third process P3), preferably in all embodiments a quotient Q is determined from the first jump ΔX1 and the second jump ΔX2. This quotient Q is processed/evaluated in order to be able to identify a foam contacting. If the quotient Q exceeds a factor F, an identifier KS is output which signals a contacting of the sensor 3 with foam 2 in the liquid container 5. In all embodiments the calculative or signal-technological generation of the quotient Q is preferably implemented in the evaluation circuit A. The factor F is used here as a specification (quantity).

Instead of working with two different identifiers Kf and Ks in all embodiments, a single identifier can be output as well which, for example, is logic "1" when foam 2 is present and logic "0" if no foam is present.

If the contacting of the sensor 3 with foam 2 has been identified, optionally in all embodiments a further "investigation" can follow whilst the sensor 3 is moved further in the previous direction in order to be able to identify a subsequent liquid boundary (located below the foam 2 during the downward movement or above the foam 2 during the upwards movement).

Optionally, in all embodiments characteristic quantities can be determined or derived from the output signal $s_{out}(t)$. In this case, for example, a first phase angle PH1 and a second phase angle PH2 or a phase shift Δφ can be determined (e.g. in a computational manner). It is then investigated whether the magnitude of the first phase angle PH1 minus the second phase angle PH2 (i.e. the phase shift Δφ) is smaller than a factor that is predefined. If this is the case, a liquid boundary was then detected. Otherwise, the more accurate investigation can be continued during the further movement of the sensor 3 until a liquid boundary was detected in the said manner. The computational or signal-technology processing of the phase angle PH1, PH2 is preferably implemented in the evaluation circuit A in all embodiments.

The evaluation after the detection of foam 2 can in all embodiments also comprise the identification of a resistance jump ΔR which occurs on transition of the sensor 3 from foam 2 into liquid 1. This resistance jump ΔR can be determined by evaluating/processing the output signal $s_{out}(t)$.

In all embodiments of the invention, the evaluation of the output signal $s_{out}(t)$ can be made at the same time (quasi in real time) as the movement B of the sensor 3.

In all embodiments of the invention, the circuit principle which forms the basis of all the circuits according to FIGS. 2 and 3 can also be reversed. In the said figures the liquid container 5 is at earth and signals (called input signals ($s_{in}(t)$)) are applied to the sensor 3. When reversing the circuit principle, the sensor 3 would be placed at earth and signals (called input signals ($s_{in}(t)$)) are applied to the liquid container 5. In this case, certain adaptations on the part of the circuits E and A are possibly required.

Alternatively circuits are also possible which do not relate to earth, as described above. Such an alternative circuit can, for example, comprise a capacitive voltage divider in the form of a measuring bridge. Such circuits are also used to realize or implement the present invention.

REFERENCE LIST

Evaluation circuit/unit A
Delivery movement B
Phase shift Δφ
Resistance jump ΔR
Input signal generator E
Factor F
First alternating voltage generator $G_1$
Second alternating voltage generator $G_2$
Alternating voltage generator G
High-pass filter HP
Low-pass filter TP
Identifier for phase boundary general KL
Identifier for foam Ks
Identifier for liquid Kf
Measuring device/setup
First process $P_1$
Second process $P_2$
Third process $P_3$
Fourth process $P_4$
Phase angle PH1, PH2
Sinusoidal signal S
First sinusoidal signal $S_1$
Second sinusoidal signal $S_2$
Voltage adder SA
Output signal $s_{out}(t)$
First output signal $s_{out1}(t)$
Second output signal $s_{out2}(t)$
Input signal $s_{in}(t)$
Jump factor SF
Time t
Amplifier V
Liquid 1
Foam 2
Sensor (pipette) 3
Liquid container 5
Second signal path 6

First signal path 7
Third signal path 6'
Fourth signal path 7'
Laboratory device 100
First frequency $f_1$
Second frequency $f_2$
First jump (property of output signal with the greater jump on contact with foam) $\Delta X1$
Second jump (property of output signal with the smaller jump on contact with foam) $\Delta X2$
Quotient (of the first capacitance jump and the second capacitance jump) Q

What is claimed is:

1. Method for distinguishing between a contacting of foam (2) or of liquid (1) in a liquid container (5) of a device (100) by means of a capacitively operating measuring device (M) having a sensor (3) which can be moved up and down in the liquid container (5), wherein at least one output signal ($s_{out}(t)$) is processed by the measuring device (M), the method comprising the following steps:
   a. executing an up or down movement (B) of the sensor (3) in the liquid container (5);
   b. applying an input signal ($s_{in}(t)$) having a first frequency (f1) to the sensor (3);
   c. applying the input signal ($s_{in}(t)$) having a second frequency (f2) to the sensor (3), where the second frequency (f2) and the first frequency (f1) are different;
   d. within the framework of a first process (P1)—evaluating the output signal ($s_{out}(t)$) in order to detect a first jump ($\Delta X1$) of the output signal ($s_{out}(t)$);
   e. within the framework of a second process (P2)—evaluating the output signal ($s_{out}(t)$) in order to detect a second jump ($\Delta X2$) of the output signal ($s_{out}(t)$),
   f. comparing the first jump ($\Delta X1$) with the second jump ($\Delta X2$);
   g. outputting an identifier (Ks, Kf) which signals a contacting of the sensor (3) with foam (2) in the liquid container (5) if the comparison exceeds a specification, and which signals a contacting of the sensor (3) with liquid (1) in the liquid container (5) if the comparison does not exceed the specification.

2. The method according to claim 1, characterized in that in step f. in the comparison, a quotient (Q) of the first jump ($\Delta X1$) and the second jump ($\Delta X2$) is determined and that in step g. a factor (F) serves as a specification, wherein the identifier (Ks, Kf) is output to signal a contacting of the sensor (3) with foam (2) in the liquid container (5) if the quotient (Q) exceeds the factor (F), and to signal a contacting of the sensor (3) with liquid (1) if the quotient (Q) does not exceed the factor (F).

3. The method according to claim 1, characterized in that a jumpy change in the output signal ($s_{out}(t)$), which reaches at least a jump factor (SF) is identified as jump ($\Delta X1$, $\Delta X2$).

4. The method according to claim 1, characterized in that:
   a first sinusoidal signal ($S_1$) having the first frequency ($f_1$) is applied within the framework of the first process (P1) as input signal ($s_{in}(t)$); and
   a second signal ($S_2$) having the second frequency ($f_2$) is applied within the framework of the second process (P2) as input signal ($s_{in}(t)$).

5. The method according to claim 4, characterized in that:
   the first sinusoidal signal ($S_1$) and the second sinusoidal signal ($S_2$) are applied in a superposed manner simultaneously as input signal ($s_{in}(t)$); and
   the output signal ($s_{out}(t)$) is divided into a first output signal component ($s_{out1}(t)$)—corresponding to the first frequency ($f_1$)—and a second output signal component ($s_{out2}(t)$)—corresponding to the second frequency ($f_2$);
   the first output signal component ($s_{out1}(t)$) is evaluated within the framework of the first process ($P_1$) and the second output signal component ($s_{out2}(t)$) is evaluated within the framework of the second process ($P_2$) preferably simultaneously.

6. The method according to claim 4, characterized in that:
   the first sinusoidal signal ($S_1$) and the second sinusoidal signal ($S_2$) are applied alternately as input signal ($s_{in}(t)$); and
   the output signal ($s_{out}(t)$) corresponding to the first frequency ($f_1$) or the second frequency ($f_2$) is evaluated alternately within the framework of the first process ($P_1$) or the second process ($P_2$).

7. The method according to claim 1, characterized in that the evaluation of the output signal ($s_{out}(t)$) comprises the determination of a phase shift ($\Delta\varphi$) of a complex permittivity which signals a contacting of the sensor (3) with a liquid (1) below foam (2) in the liquid container (5).

8. The method according to claim 1, characterized in that after output of the identifier (Ks) which signals a contacting of the sensor (3) with foam (2), the following steps are carried out:
   a. executing a further movement (B) of the sensor (3) in the previously executed direction of movement;
   b. within the framework of a fourth process ($P_4$)—applying an input signal ($s_{in}(t)$) to the sensor (3) and evaluating the output signal ($s_{out}(t)$), in order to detect a foam-liquid phase boundary and optionally output an identifier (Kf) which signals a transition of the sensor (3) from foam (2) into liquid (1).

9. The method according to claim 8, characterized in that: the evaluation of the output signal ($s_{out}(t)$) within the framework of the fourth process ($P_4$) comprises the evaluation or processing of a complex permittivity.

10. The method according to claim 8, characterized in that when evaluating within the framework of the fourth process ($P_4$) a difference between two phase angles (PH1, PH2) in terms of magnitude or a phase shift ($\Delta\varphi$) is determined in order to then output an identifier (Kf) which signals a transition of the sensor (3) from foam (2) into liquid (1).

11. Apparatus which is equipped with a capacitively operating measuring device (M) for distinguishing between a contacting of foam (2) or of liquid (1) in a liquid container (5), wherein the apparatus comprises a movable sensor (3), an input signal generator (E) and an evaluation circuit (A), wherein the input signal generator (E) is connectable in terms of circuitry to the sensor (3) or to the liquid container (5) and wherein the evaluation circuit (A) is connectable in terms of circuitry to the sensor (3) or to the liquid container (5) so that the output signal ($s_{out}(t)$) is processable by the evaluation circuit (A), characterized in that the input signal generator (E)
   is configured to be able to determine the capacitance of the sensor (3) at a first frequency ($f_1$) and at a second frequency ($f_2$), where the second frequency ($f_2$) and the first frequency ($f_1$) are different,
   and in that the evaluation circuit (A)
   is configured to evaluate the output signal ($s_{out}(t)$) in order to detect a first jump ($\Delta X1$) of the output signal ($s_{out}(t)$) and a second jump ($\Delta X2$) of the output signal ($s_{out}(t)$);
   is configured to compare the first jump ($\Delta X1$) with the second jump ($\Delta X2$);
   is configured to output an identifier (Ks Kf) which signals a contacting of the sensor (3) with foam (2) in the liquid container (5) if the comparison exceeds a specification, and which signals a contacting of the sensor (3) with liquid (1) in the liquid container (5) if the comparison does not exceed the specification.

12. The apparatus according to claim 11, characterized in that it is configured to form a quotient (Q) of the first jump ($\Delta X1$) and the second jump ($\Delta X2$) when comparing and to output the identifier (Ks Kf) to signal a contacting of the sensor (3) with foam (2) in the liquid container (5) if the quotient (Q) exceeds a factor (F) serving as a specification, and to signal a contacting of the sensor (3) with liquid (1) if the quotient (Q) does not exceed the factor (F).

13. The apparatus according to claim 11, characterized in that the input signal generator (E) is configured to provide two signals ($S_1$, $S_2$) which can be combined to produce a combined alternating voltage, wherein preferably a voltage adder (SA) is used to produce a combined alternating voltage which serves as input signal ($s_{in}(t)$).

14. The apparatus according to claim 11, characterized in that the evaluation circuit (A) comprises a diplexer (TP, HP) which is configured to divide the output signal ($s_{out}(t)$) into a first output signal ($s_{out1}(t)$) and a second output signal ($s_{out2}(t)$), wherein the first output signal ($s_{out1}(t)$) and the second output signal ($s_{out2}(t)$) are evaluable by the evaluation circuit (A).

15. The apparatus according to claim 14, characterized in that the evaluation circuit (A) is configured to determine a phase shift ($\Delta\varphi$) of a complex permittivity which signals a contacting of the sensor (3) with a liquid (1) below or above foam (2) in the liquid container (5).

* * * * *